United States Patent [19]

Sabelman et al.

[11] Patent Number: 4,465,478
[45] Date of Patent: Aug. 14, 1984

[54] SYRINGE FORCE AMPLIFICATION DEVICE

[75] Inventors: Eric E. Sabelman, Menlo Park; Timothy A. Koogle, Redwood City; William Kennedy, Palo Alto, all of Calif.

[73] Assignee: Collagen Corporation, Palo Alto, Calif.

[21] Appl. No.: 434,223

[22] Filed: Oct. 14, 1982

[51] Int. Cl.³ .............................................. A61M 5/00
[52] U.S. Cl. .................................................. 604/224
[58] Field of Search ............... 604/224, 220, 209, 218; 222/386, 390, 391

[56] References Cited

U.S. PATENT DOCUMENTS

| 780,147 | 1/1905 | Wilcox et al. | 604/224 |
|---|---|---|---|
| 854,399 | 5/1907 | Bridge | 604/224 |
| 1,718,596 | 6/1929 | Smith . | |
| 1,798,116 | 3/1931 | Brockway | 604/220 |
| 1,823,654 | 9/1931 | Hast . | |
| 2,316,095 | 4/1943 | Mead, Jr. . | |
| 2,491,978 | 12/1949 | Helfman et al. . | |
| 2,853,070 | 9/1958 | Julliard . | |
| 2,892,457 | 6/1959 | Sturtz . | |
| 3,212,685 | 10/1965 | Swan et al. . | |
| 3,720,211 | 3/1973 | Kyrias . | |
| 3,797,487 | 3/1974 | Schmidt . | |
| 4,231,368 | 11/1980 | Becker | 604/224 |

Primary Examiner—John D. Yasko
Attorney, Agent, or Firm—Ciotti & Murashige

[57] ABSTRACT

A syringe assist device including a frame and moveable carriage that are respectively attached to a conventional syringe and its plunger. The frame has a toothed rack and the carriage contains a force amplifying gear and lever mechanism. A thumb ring transmits the force applied by the user's thumb to the lever to rotate the gear and move the carriage along the frame. This action in turn applies amplified compression to the syringe plunger. A ratchet connection between the lever and the gear enables the movement of the carriage to be continued without force amplification when the lever has reached the end of its stroke.

14 Claims, 5 Drawing Figures

SYRINGE FORCE AMPLIFICATION DEVICE

TECHNICAL FIELD

The present invention is directed to a device for amplifying the mechanical force applied to a syringe to compress the plunger into the barrel of the syringe with a fine degree of control.

BACKGROUND ART

Most liquid medicines and the like that are typically injected with a syringe have a sufficiently low viscosity that the plunger of the syringe can be manually compressed into its barrel, to expel the liquid therefrom, with relatively little effort. However, when a high viscosity material is to be injected, particularly through a hypodermic needle having a small opening, difficulties are presented. As the force required to move the plunger increases, the degree of control that can be exercised over the rate of injection is lessened. For materials having extremely high viscosity, such as a collagen implant for example, the force required to move the plunger approaches the maximum force available to finger and thumb muscles that is consistent with fine motor control.

In the past, most devices for assisting the compression of a syringe have been relatively complex and often obstruct the view of the needle or otherwise pose difficulties relative to conventional injection techniques. One type of device comprises a pistolgrip pawl and ratchet mechanism. A drawback associated with this type of device is that the advance of the plunger is limited to steps of a fixed size, as determined by the ratchet mechanism. Consequently, the degree of control that is available is limited. In addition, most commercially available devices of this type are adapted for relatively large syringes, and are not suited for use with smaller syringes having a capacity of 1-3 cc., for example.

Other types of devices are not suited for use with conventional syringes. For example, one pneumatic syringe assist device requires a syringe that does not have a plunger, so that the compressed air can act directly on the material to be injected.

OBJECTS OF THE INVENTION

Accordingly it is a general object of the present invention to provide a novel device for amplifying the manual force that is applied to the plunger of a syringe during injection of a liquid material.

It is a more specific object of the present invention to provide a novel device that utilizes a mechanical advantage to amplify the force applied to a syringe plunger.

It is another object of the present invention to provide such a device that does not obstruct the view of the needle, to possibly limit injection sites, or otherwise interfere with the injection process.

It is a further object of the present invention to provide such a device that retains, and possibly even enhances, the tactile feedback that is provided to the person operating the syringe.

It is yet another object of the invention to provide a novel syringe force amplifying device that retains the ability to operate the syringe with the familiar and comfortable hand position that is normally utilized.

It is still a further object of the invention to provide such a device that can accomodate variations in hand size, strength and holding style.

Still another object of the invention is to provide a novel syringe force amplifying device that is both rugged and simple to construct.

Yet a further object of the invention is to provide a force amplification device that can be readily used with conventional syringes.

DISCLOSURE OF THE INVENTION

In accordance with the present invention, these and other objects are achieved, and their attendant advantages are provided, by a syringe assist device including a frame and moveable carriage that are respectively attached to a conventional syringe and its plunger. The frame has a toothed rack and the carriage contains a force amplifying gear and lever mechanism. A thumb ring transmits the force applied by the user's thumb to the lever to rotate the gear and move the carriage along the frame. This action in turn applies amplified compression to the syringe plunger. A ratchet connection between the lever and the gear enables the movement of the carriage to be continued when the lever has reached the end of its stroke.

Further features and advantages of the invention are described in greater detail hereinafter with particular reference to a preferred embodiment of the invention illustrated in the accompanying drawings.

MODES FOR CARRYING OUT THE INVENTION

Figure 1:
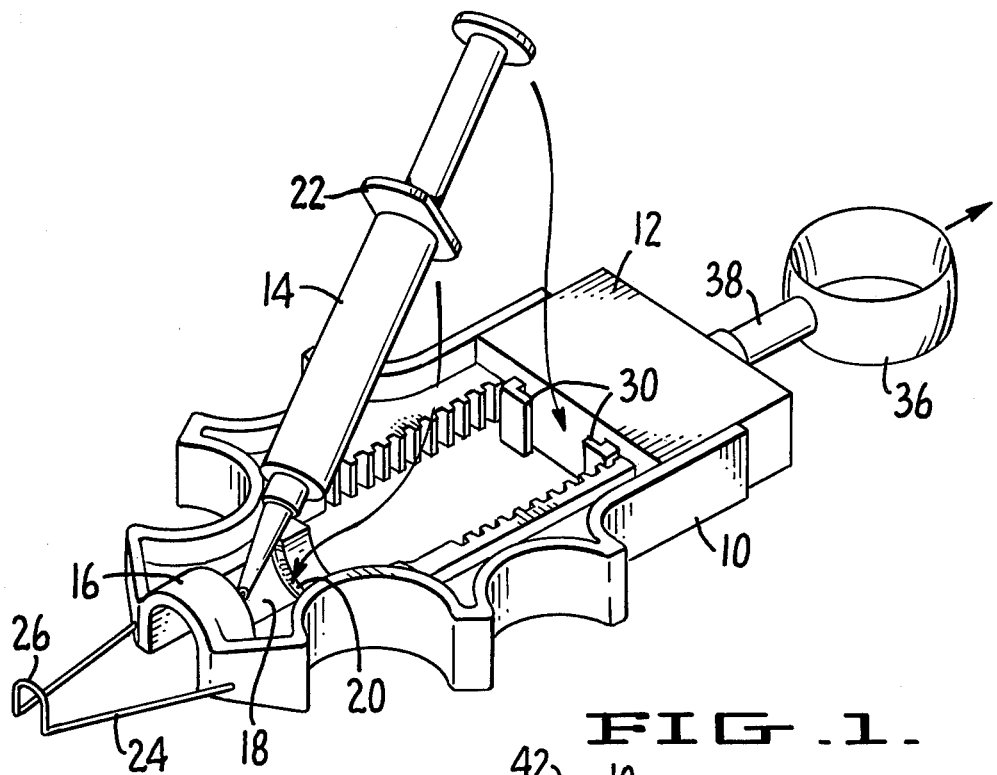
FIG. 1 is a perspective view of the syringe assist device, illustrating the manner that a syringe is inserted to be connected thereto.
Figure 2:
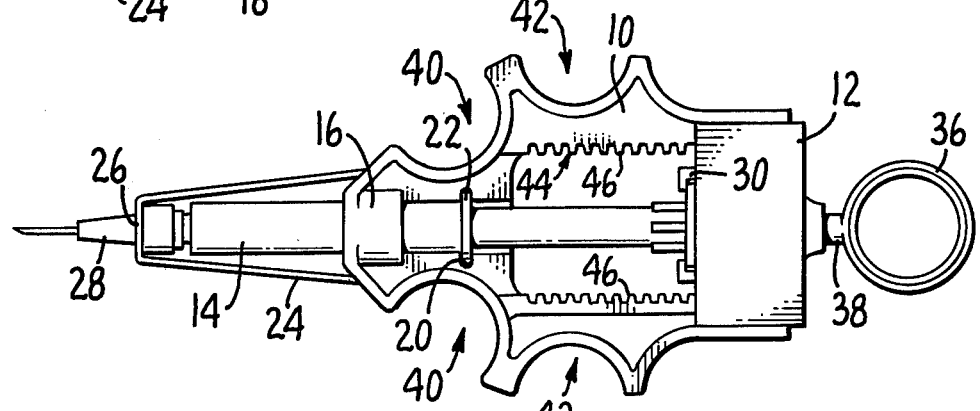
FIG. 2 is a top view of the device with a syringe inserted.
Figure 3:
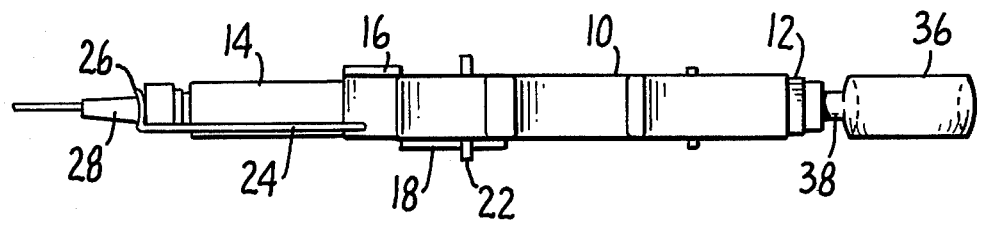
FIG. 3 is a side view of the device with a syringe inserted.

Referring to FIGS. 1-3, a syringe assist device constructed in accordance with the present invention basically comprises a frame 10 and a carriage 12 that is moveable along the frame. The forward end of the frame has a bore that accomodates the barrel 14 of a syringe. This bore is defined by an upper arc-shaped bridge 16 at the forwardmost end of the frame, and a lower arc-shaped bridge 18 disposed behind the upper bridge 16. The spacing of the bridges in this manner allows the syringe to be inserted into the bore at an angle, as depicted in FIG. 1. The lower bridge 18 is provided with a slot 20 to accomodate the flange 22 that is typically located at the top of the barrel, and thereby holds the syringe in place on the frame.

A spring clip 24 projects from the front of the frame, and includes an arcuate portion 26 at its forwardmost end that is snapped in place around the needle luer hub 28 of the syringe once it is inserted into the frame. The spring clip not only serves to secure the attachment of the syringe to the frame, but it also retains the needle in place and prevents its detachment, for example due to needle hub or syringe failure under high internal pressure.

The carriage 12 includes a pair of clips 30 that accomodate the disk-type flange 32 at the end of the syringe plunger 34, to thereby secure the plunger to the carriage. Thus, when the syringe is inserted into the frame with its flange 22 disposed in the slot 20 and the plunger is engaged in the clip 30, any movement of the carriage 12 relative to the frame will induce corresponding movement of the plunger relative to the barrel 14 of the syringe.

To enable the syringe assist device to be operated with the same one-handed holding style that is typically utilized with syringes, a thumb ring 36 is disposed on the end of a plunger 38 that projects from the rear of the carriage 12. Two pairs of finger grips 40 and 42 are provided on the frame. The two pairs of grips are displaced along the length of the frame to thereby accomodate different hand sizes and different holding styles. Thus the device can be held by placing the index and middle fingers of the hand in one of the pairs of grips and placing the thumb in the ring 36. The plunger 38 is translated into and out of the carriage with the thumb ring, utilizing the same motion as is employed with a syringe by itself.

Figure 4:
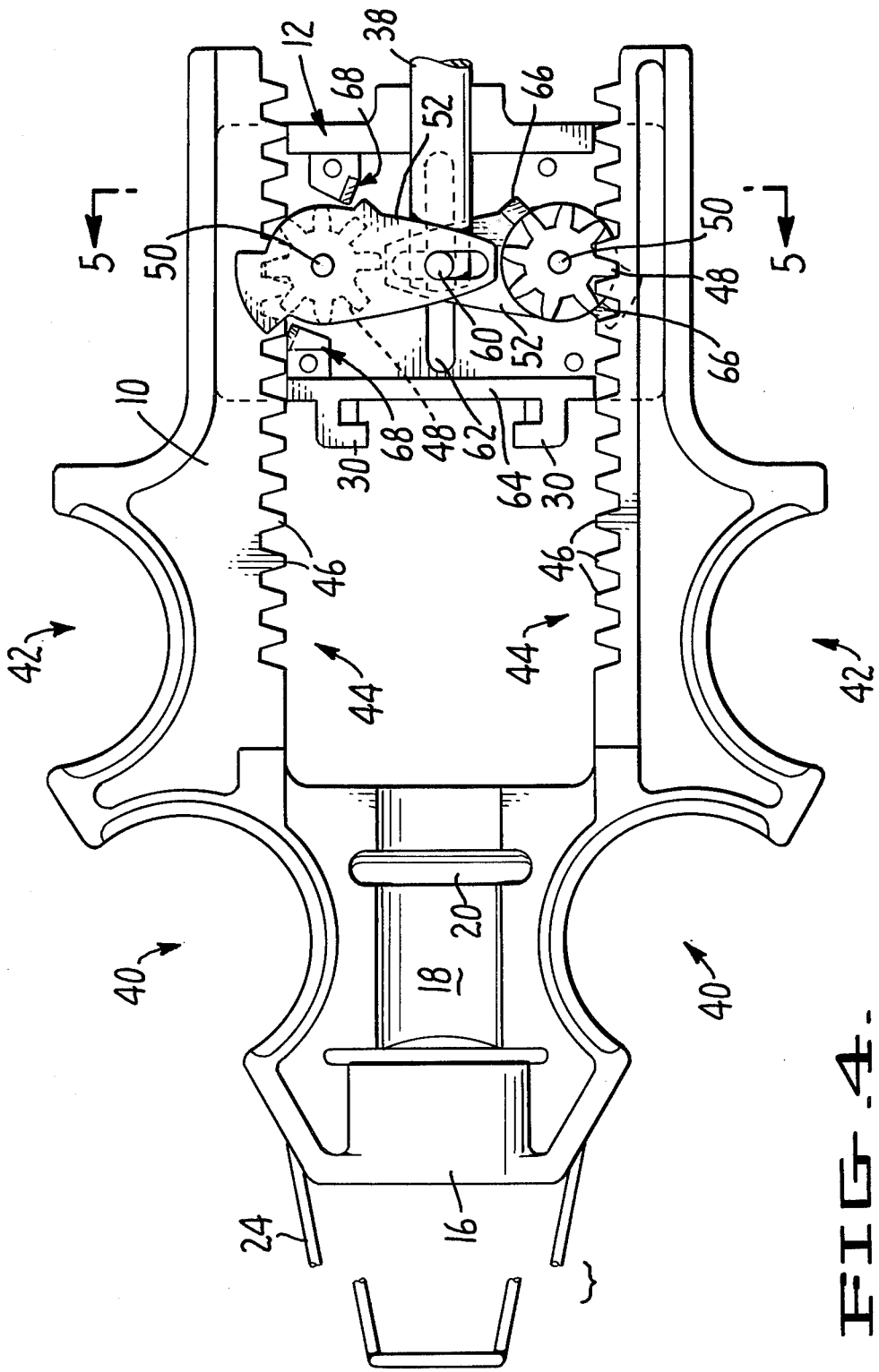
FIG. 4 is an enlarged top view of the frame and carriage with the top half of the carriage removed to illustrate the gear and lever mechanism.
Figure 5:
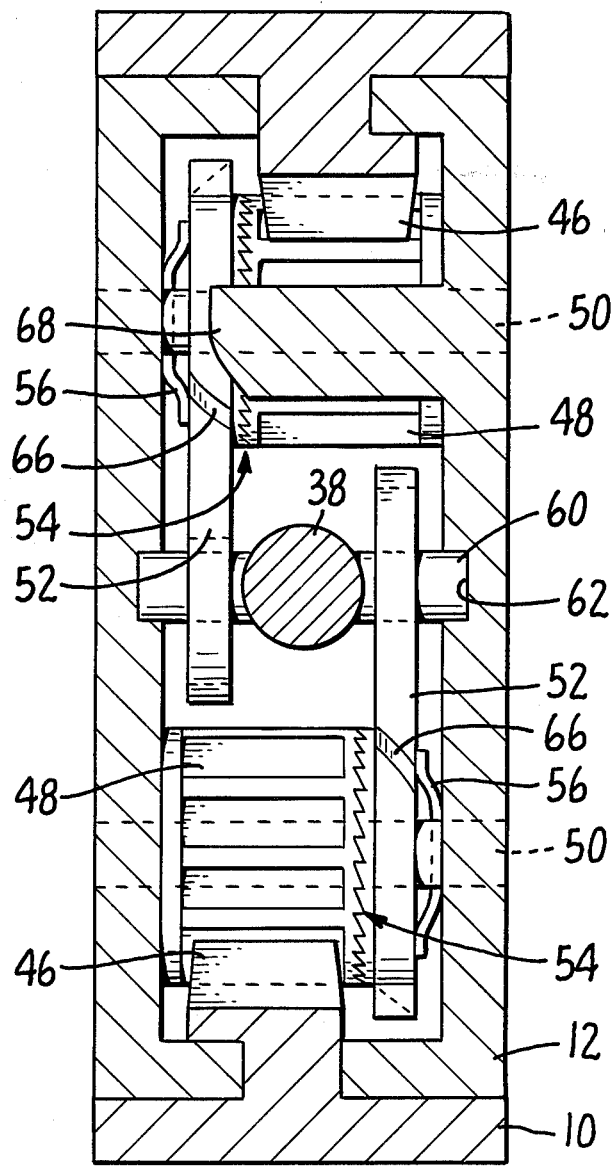
FIG. 5 is a cross-sectional end view of the frame and carriage, taken along the section line 5—5 of FIG. 4.

The manner in which the device operates to amplify the force that is manually applied to the thumb ring is explained with reference to the detailed diagrams of FIGS. 4 and 5. For ease of manufacture and assembly of the device, the carriage 12 can be made of two halves that are fitted together. The carriage is shown with the top half removed in FIG. 4.

The frame 12 is provided with two opposed parallel racks 44 having teeth 46. Two pinion gears 48 rotate about shafts 50 within the carriage, and their teeth respectively mesh with those of the racks 44. A lever 52 is disposed on each shaft 50 for limited pivotal movement. As best illustrated in FIG. 5, each lever 52 is engaged with its associated pinion gear 48 by means of ratchet teeth 54 disposed on the opposing faces of the lever and the gear. These teeth have one face that is parallel to the axis of the shafts 50, and another face that is disposed approximately 45° relative thereto. Thus, when the levers are pivoted in one direction, the pinion gears will be forced to rotate therewith. The ratchet teeth are set up so that this occurs when the levers are moved forward, i.e., the lower lever in FIG. 4 pivots in a counterclockwise direction and the upper lever moves in a clockwise direction. However, in the other direction of movement, relative rotation is allowed to take place between each lever and pinion gear by the slanted surfaces of the ratchet teeth. The levers 52 are biased in an axial direction into normal engagement with the pinion gears by means of springs 56, for example spring washers.

The ends of the levers 52 that are remote from the shafts 50 include slots 58 that accomodate a shaft 60. The shaft 60 is parallel to the gear shafts 50, and is translatable in a transverse direction within two recesses 62 in the carriage 12. Translation of the shaft 60, and hence pivoting of the levers 52, is provided by the plunger 38, which is rigidly connected to the shaft.

The moment arm, or operative length, of each lever 52, i.e., the distance between the axes of the shafts 50 and 60, is greater than that of the gear which it engages, i.e., greater than the distance between the axis of the shaft 50 and the point of engagement between the gear teeth and the rack teeth 46. Thus, the gear and lever arrangement provides a mechanical advantage with respect to force applied through the plunger 38. Preferably, the levers and gears are dimensioned so that the carriage moves along the frame with a force that is four times greater than that applied to the thumb ring 36 and plunger 38.

In operation, the thumb ring 36 is pulled to move the carriage to the right (as viewed in FIG. 4), and a syringe is inserted in the device in the manner illustrated in FIG. 1. The plunger flange 32 is engaged in the clips 30 of the carriage, and the retainer 26 snapped in place around the needle hub, to attach the syringe to the device as shown in FIGS. 2 and 3. Thereafter, as the thumb ring is pushed into the carriage, the levers 52 and gears 48 will be pivoted about the shafts 50, causing the carriage to move forward along the frame and compress the plunger into the barrel 14 with a greater force than that applied by the thumb to the ring. Conversely, the carriage will move a proportionately shorter distance than the thumb ring.

At the end of travel of the thumb ring, i.e., when the levers 52 contact the front wall 64 of the carriage, the carriage can continue to move forward under direct pressure from the thumb if no mechanical advantage is required. In this case, the ratchet teeth 54 will enable the pinion gears 48 to continue turning as the carriage moves along the frame, even though the levers are stationary.

Alternatively, if force amplification is required to continue the movement of the plunger, the thumb ring is retracted to pull the plunger out of the carriage. In this case, the carriage will remain stationary due to the dampening effect provided by the syringe, i.e., the plunger will resist being pulled from the barrel. Again, the ratchet teeth will allow relative rotation between the levers and the gears, enabling the levers to be pivoted rearwardly while the gears remain motionless. The thumb ring can then be pressed towards the carriage again, providing continued forward movement of the carriage with force amplification.

In order to enable the carriage to be retracted, a pair of cam surfaces 66 are provided on each lever 52. These cam surfaces are disposed at an appropriate angle, e.g., 45°, relative to the axis of the shafts 50. A pair of corresponding cams 68 are provided on the carriage adjacent each lever (only two of which are illustrated in FIG. 4 adjacent the upper lever). As the levers 52 approach the limit of their travel when the thumb ring is pulled away from the carriage, the cam surfaces 66 will engage and ride up on the cams 68, causing the levers to move axially against the bias of the springs 56. Consequently, the ratchet mechanisms will be disengaged, enabling the pinion gears to rotate freely. Thus, the entire carriage will be retracted if the thumb ring continues to be pulled outwardly.

From the foregoing, it can be seen that the present invention provides a device that amplifies the manual force applied to a syringe while retaining the ability to operate the syringe in a conventional fashion and without obstruction. Precise control over the amount and rate of compression of the syringe is afforded, along with tactile feedback as to the resistance offered by the syringe.

It will be appreciated by those of ordinary skill in the art that the present invention can be embodied in other specific forms without departing from the spirit or essential characteristics thereof. The presently disclosed embodiment is therefore considered in all respects to be illustrative and not restrictive. The scope of the invention is indicated by the appended claims rather than the foregoing description, and all changes that come within the meaning and range of equivalents thereof are intended to be embraced therein.

We claim:

1. Apparatus for amplifying the manual force applied to compress the plunger of a syringe into its barrel, comprising:

a frame having means for attachment to the barrel of a syringe;

a carriage mounted on said frame so as to be moveable relative thereto along the longitudinal axis of a syringe attached to the frame, said carriage including means for engaging the plunger of a syringe;

a gear rotatably mounted on said carriage and operatively engaging said frame such that rotation of said gear induces movement of said carriage along said axis; and manually actuatable means for rotating said gear with a mechanical advantage such that the linear force applied to the plunger of a syringe connected to said carriage is greater than the force that is manually applied to rotate said gear.

2. The apparatus of claim 1 wherein said manually actuatable means includes a pivotable lever operatively engaged for rotation with said gear, and means for applying a linear force to the end of said lever that is remote from its pivot axis, said lever having a greater moment arm than said gear.

3. The apparatus of claim 2 wherein said lever is engaged with said gear by means of a ratchet arrangement that enables relative rotation between said lever and said gear in one direction.

4. The apparatus of claim 3 further including means for disengaging said lever from said gear near one end of the pivot stroke of said lever, to thereby permit relative rotation of said lever and said gear in the other direction.

5. The apparatus of claim 1 wherein said frame includes finger grips for grasping by at least two fingers of a person operating a syringe, and said manually actuatable means includes a thumb ring to accomodate the thumb of the person.

6. The apparatus of claim 5 wherein two pairs of finger grips are provided on said frame at different locations along its length to accomodate different hand sizes and holding styles.

7. The apparatus of claim 1 wherein said frame further includes a retainer for attachment to the needle of a syringe.

8. A device for increasing the compressive force that is manually applied to a syringe, comprising:

a frame having means for attachment to the barrel of a syringe and including a pair of opposed racks of teeth;

a carriage mounted for movement between said racks of teeth along a path of travel parallel thereto, said carriage having means for engaging the plunger of a syringe attached to said frame;

a pair of pinion gears rotatably disposed on said carriage and respectively engaging said racks of teeth;

a pair of levers respectively engaged for rotation with said pinion gears, each of said levers having an operative length greater than the radius of its associated pinion gear to thereby provide a mechanical advantage; and a plunger connected to said levers and adapted to be manually translated to pivot said levers and thereby move said carriage relative to said frame due to the interaction between the rotating gears and the rack teeth.

9. The device of claim 8 wherein said levers are engaged with their respective pinion gears by means of ratchet arrangements that enable relative rotation to take place between said levers and their respective gears in one direction.

10. The device of claim 9 further including means for disengaging said levers from said gears near one end of the pivot stroke of said levers, to thereby permit relative rotation of said levers and said gears in the other direction.

11. The device of claim 8 wherein said plunger includes a ring disposed at the end thereof that is remote from its connection to said levers, said ring being adapted to accomodate the thumb of a user.

12. The device of claim 11 wherein two pairs of finger grips are provided on said frame at different locations along its length to accomodate different hand sizes and holding styles.

13. The device of claim 8 wherein said frame further includes a retainer for attachment to the needle of a syringe.

14. Apparatus for amplifying the manual force applied to compress the plunger of a syringe into its cylinder, comprising:

a frame having means for attachment to the barrel of a syringe;

a carriage mounted on said frame so as to be moveable relative thereto and including means for engaging the plunger of a syringe attached to said frame;

means adapted to be manually moved to apply a linear force to said carriage; and means operatively disposed between said force applying means and said frame for moving said carriage along said frame with a mechanical advantage such that the force applied to the plunger of a syringe by said carriage is greater than the manual force applied to said force applying means.

* * * * *